United States Patent [19]

Schnurr et al.

[11] Patent Number: 5,466,831
[45] Date of Patent: Nov. 14, 1995

[54] PREPARATION OF 3-(2-ACYLOXYETHYL)-DIHYDRO-2(3H)-FURANONES

[75] Inventors: Werner Schnurr, Herxheim; Rolf Fischer, Heidelberg; Norbert Goetz, Worms; Thomas Kuekenhoehner, Boehl-Iggelheim, all of Germany

[73] Assignee: BASF Aktiengesellschaft, Ludwigshafen, Germany

[21] Appl. No.: 99,232

[22] Filed: Jul. 29, 1993

[30] Foreign Application Priority Data

Aug. 28, 1992 [DE] Germany .............. 42 28 668.9

[51] Int. Cl.[6] ................................. C07D 307/12
[52] U.S. Cl. ......................................... 549/323
[58] Field of Search ................................. 549/323

[56] References Cited

U.S. PATENT DOCUMENTS

| | | | |
|---|---|---|---|
| 3,510,511 | 5/1970 | Conseiller et al. | 560/157 |
| 4,734,521 | 3/1988 | Frazier | 560/157 |
| 4,831,166 | 5/1989 | Eckhardt et al. | 549/323 |
| 4,837,346 | 6/1989 | Becker et al. | 549/425 |

FOREIGN PATENT DOCUMENTS 1493211  6/1969  Germany.

OTHER PUBLICATIONS

Ganem et al, Journal of Organic Chemistry, vol. 39, No. 25 (1974), pp. 3728–3730.

*Primary Examiner*—C. Warren Ivy
*Assistant Examiner*—Raymond Covington
*Attorney, Agent, or Firm*—John H. Shurtleff

[57] ABSTRACT

A process for the preparation of 3-(2'-acyloxyethyl)-dihydro-2(3H)furanones of the general formula I

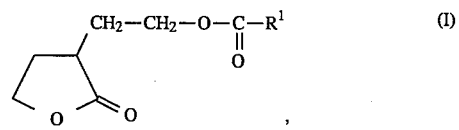

in which $R^1$ denotes $C_1$–$C_{12}$ alkyl, $C_5$–$C_8$ cycloalkyl, aryl, $C_7$–$C_{12}$ aralkyl, or $C_7$–$C_{12}$ alkylaryl, in which a 3-(2'-oxyethyl)-dihydro-2(3H)furanone of the general formula II

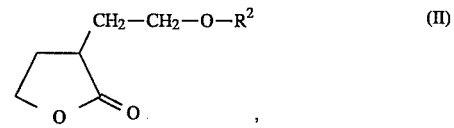

in which $R^2$ denotes $C_1$–$C_{12}$ alkyl, $C_5$–$C_8$ cycloalkyl, aryl, $C_7$–$C_{12}$ aralkyl, or $C_7$–$C_{12}$ alkylaryl is caused to react with a carboxylic acid, a carboxylic anhydride, and/or an acyl halide in the presence of an acid catalyst at temperatures of from 50° to 250° C. and pressures of from 0.1 to 100 bar.

11 Claims, No Drawings

PREPARATION OF 3-(2-ACYLOXYETHYL)-DIHYDRO-2(3H)-FURANONES

The present invention relates to a process for the preparation of 3-(2'-acyloxyethyl)-dihydro- 2(3H )furanones by the reaction of 3-(2'-oxyethyl )-dihydro- 2(3H)furanones with carboxylic acids, carboxylic anhydrides, and acyl chlorides in the presence of acidic catalysts.

EP-A 284,969 (U.S. Pat. No. 4,837,346) discloses that it is possible to prepare tetrahydropyran-4-carboxylates by the reaction of 3-(2'-hydroxyethyl)-dihydro-2(3H)furanone or esters thereof with alcohols in the presence of acidic catalysts. This reaction produces 3-(2'-alkoxyethyl)-dihydro-2(3H)furanones as by-products. These ethers can also be converted to tetrahydropyran-4-carboxylates by recycling. Nevertheless, the tetrahydropyran-4-carboxylate yields here attained are well below the values of the aforementioned reaction.

It is also known in the art that ethers can be reacted with carboxylic acids or carboxylic anhydrides over acid catalysts (e.g., in DE-A 1,493,211 over aluminum silicates; in NL-A 6,707,444 over sulfuric acid; and in U.S. Pat. No. 4,734,521 over sulfonic acids on polymeric supports/Cu(I)Cl) to form carboxylates.

It was to be expected that under the said drastic reaction conditions 3-(2'-alkoxyethyl)-dihydro- 2(3H)furanones form elimination products as by-products to an increasing extent.

It is thus an object of the present invention to overcome the aforementioned drawbacks.

Accordingly, we have found a novel and improved process for the preparation of a 3-(2'-acyloxyethyl)-dihydro-2(3H)furanone of the general formula I

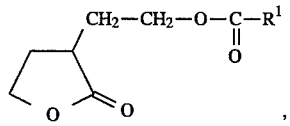

in which $R^1$ denotes $C_1$–$C_{12}$ alkyl, $C_5$–$C_8$ cycloalkyl, aryl, $C_7$–$C_{12}$ aralkyl, or $C_7$ –$C_{12}$ alkylaryl, wherein a 3-(2'-oxyethyl)-dihydro-2(3H)furanone of the general formula II

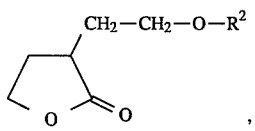

in which $R^2$ denotes $C_1$–$C_{12}$ alkyl, $C_5$–$C_8$ cycloalkyl, aryl, $C_7$–$C_{12}$ aralkyl, or $C_7$ –$C_{12}$ alkylaryl is caused to react with a compound bearing the acyl group $R^1CO$—, where $R^1$ has the meanings given above, and being selected from the group consisting of carboxylic acids, carboxylic anhydrides and acyl halides, in the presence of an acid catalyst at a temperature of from 50° to 250° C. and a pressure of from 0.1 to 100 bar.

The process of the invention may be carried out as follows:

The 3-(2'-oxyethyl)-dihydro-2(3H)furanones II can be admixed with carboxylic acids, carboxylic anhydrides, and/or acyl halides in the presence of acid catalysts, and the mixture may then be caused to react at elevated temperatures.

The reaction can be carried out at temperatures of from 50° to 250° C. and preferably at from 100° to 200° C. and pressures of from 0.1 to 100 bar and especially from 1 to 10 bar.

The reaction can be carried out batchwise or continuously as a fixed bed reaction using fixed bed catalysts, for example, in a packed bubble column or a trickle bed reactor, or alternatively using fixed bed catalysts suspended in the liquid phase. Another alternative is to use acid catalysts homogeneously dissolved in the liquid phase.

If the carboxylate formed from the liberated alcohol and excess carboxylic acid boils at a temperature below the boiling point of the carboxylic acid used, it may be advantageous to remove the carboxylate continuously from the reaction mixture, e.g., by distillation.

Suitable 3-(2'-oxyethyl)-dihydro-2(3H)furanones, all of which are ethers, are, for example, methoxy-, ethoxy-, propoxy-, butoxy-, and tert.-butoxy-ethyldihydro-2(3H)furanones.

Suitable carboxylic acids are, e.g., formic acid, acetic acid, propionic acid, butyric acid, cyclohexanoic acid, and benzoic acid, and suitable anhydrides are, e.g., acetic anhydride, glutaric anhydride, and benzoic anhydride. Suitable acyl halides are, e.g., acetyl chloride, propionyl chloride, butyryl chloride, and benzoyl chloride.

The molar ratio of acid, anhydride, or acyl halide to the ether II is advantageously from 1:1 to 10:1 and especially 1.5:1.

Suitable acid or superacid catalysts are, e.g., mineral acids such as sulfuric acid or phosphoric acid, sulfonic acids such as toluenesulfonic acid or fluorosulfonic acid, zeolites, e.g., those having a pentasile structure such as ZSM-5 or ZSM-11, alumosilicates such as Tonsil, heteropoly acids such as $H_3PW_{12}O_{40}$ or $Cs_{2.5}H_{0.5}PW_{12}O_{40}$, ion exchangers such as perfluoroalkylsulfonic acids (e.g. Nafion®, a product of Du Pont de Nemours, E.I. & Co.) or sulfonic acids attached to polymeric supports (e.g., Amberlyst), Lewis acids such as zinc chloride or copper chloride and acidic oxides such as silicon dioxide, titanium dioxide, zirkonium dioxide, or aluminum oxide and preferably mineral acids, sulfonic acids, zeolites, ion exchangers, and heteropoly acids and more preferably sulfuric acid, zeolites, toluenesulfonic acid, and ion exchangers.

The substituents $R^1$ and $R^2$ in the compounds I and II have the following meanings:

$R^1$, $R^2$ individually denote $C_1$–$C_{12}$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl, and isododecyl and preferably $C_1$–$C_8$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl and more preferably $C_1$–$C_4$ alkyl such as methyl, ethyl, n-propyl, isopropyl, n-butyl, isobutyl, sec-butyl, and tert-butyl, $C_5$–$C_8$ cycloalkyl such as cyclopentyl, cyclohexyl, cycloheptyl, and cyclooctyl and preferably cyclopentyl, cyclohexyl, and cyclooctyl and more preferably cyclopentyl and cyclohexyl aryl such as phenyl, 1-naphthyl, 2-naphthyl, 1-anthryl, 2-anthryl, and 9-anthryl and preferably phenyl, 1-naphthyl, and 2-naphthyl and more preferably phenyl, C$_7$–C$_{12}$ aralkyl and preferably C$_7$–C$_{12}$ phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl, and 4-phenylbutyl and more preferably benzyl, 1-phenethyl, and 2-phenethyl, C$_7$–C$_{12}$ alkylaryl and preferably C$_7$–C$_{12}$ alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl, and 4-n-propylphenyl.

The process of the invention can convert the most important by-product of the tetrahydropyran-4-carboxylate synthesis, i.e. 3-(2'-methoxyethyl)-dihydro-2(3H)furanone, to the educt 3-(2'-acetoxyethyl)-dihydro-2(3H)furanone so that it can be recycled to the tetrahydropyran-4-carboxylate synthesis.

EXAMPLES

Example 1

In a stirred vessel there is heated to 120° C. a mixture of 20 g of 3-(2'-methoxyethyl)-dihydro- 2(3H)furanone, 100 g of glacial acetic acid, and 10 g of Nafion. Following a period of 69 h, the reaction is terminated (conversion: 89%) and the catalyst is separated by filtration. Following purification by distillation, there is obtained 65% of 3-(2'-acetoxyethyl)-dihydro-2(3H)furanone (based on the 3-( 2'-methoxyethyl)-dihydro-2(3H)furanone used).

Example 2

In a stirred vessel, a mixture of 10 g of 3-(2'-methoxyethyl)-dihydro-2(3H)furanone, 10 g of glacial acetic acid, and 1 g of conc. sulfuric acid is heated to 180° C. Following a period of 19 h, the reaction is terminated. The effluent consists of the following (in percent by area as determined by GC-Analysis): 86% of 3-(2'-acetoxyethyl)-dihydro-2(3H)furanone and 11% of 3-(2'-methoxyethyl)-dihydro-2(3H )furanone.

Example 3

In a stirred vessel there is heated to 150° C. a mixture of 72 g of 3-(2'-methoxyethyl)-dihydro- 2(3H)furanone, 90 g of glacial acetic acid, and 14 g of zeolite (ZSM-11). Following a period of 24 h, the reaction is terminated and the catalyst separated by filtration. The effluent consists of the following (in percent by area as determined by GC-Analysis): 75% of 3-(2'-acetoxyethyl)-dihydro- 2(3H)furanone, 9% of 3-(2'-hydroxyethyl)-dihydro-2(3H)furanone and 9% of 3-( 2'-methoxyethyl)-dihydro-2(3H )furanone.

Example 4

In a stirred vessel, a mixture of 20 g of 3-(2'-methoxyethyl)-dihydro-2(3H)furanone, 100 g of acetic anhydride, and 10 of Nafion is heated to 120° C. Following a period of 69 h, the reaction is terminated (conversion: 100%) and the catalyst is separated by filtration. Following purification by distillation, there is obtained 61% of 3-(2'-acetoxyethyl)-dihydro-2(3H)furanone.

Example 5

In a stirred vessel, a mixture of 10 g of 3-(2'-tert-butoxyethyl)-dihydro-2(3H)furanone, 50 g of glacial acetic acid, and 5 g of Nafion is heated to 120° C. Following a period of 19 h, the reaction is terminated (conversion: 100%) and the catalyst is separated by filtration. Following purification by distillation, there is obtained 98% of 3-(2'-acetoxyethyl)-dihydro-2(3H)furanone.

Example 6

In a stirred vessel, a mixture of 10 g of 3-(2'-methoxyethyl)-dihydro-2(3H)furanone, 20 g of propionic acid, and 5 g of zeolite (ZSM-11) is heated to 150° C. Following a period of 20 h, the reaction is terminated and the catalyst separated by filtration. The effluent consists of the following (in percent by area as determined by GC-Analysis): 84% of 3-(2'-propionoxyethyl)-dihydro-2(3H)furanone, 7% of 3-( 2'-hydroxyethyl)-dihydro-2(3H)furanone and 7% of 3-(2'-methoxyethyl)-dihydro- 2(3H)furanone.

Example 7

In a stirred vessel, a mixture of 10 g of 3-(2'-methoxyethyl)-dihydro-2(3H)furanone, 40 g of cyclohexanoic acid, and 5 g of zeolite (ZSM-11) is heated to 150° C. Following a period of 25 h, the reaction is terminated and the catalyst separated by filtration. The effluent consists of the following (in percent by area as determined by GC-Analysis): 66% of ester I, 4% of 3-(2'-hydroxyethyl)dihydro- 2(3H)furanon, and 11% of 3-(2'-methoxyethyl)-dihydro-2(3H)furanone.

We claim:

1. A process for the selective preparation in high yields of at least 65% of a 3- (2'-acyloxyethyl)-dihydro-2(3H)furanone of the formula

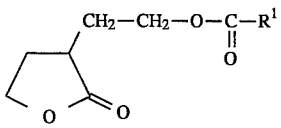

in which R$^1$ denotes C$_1$–C$_{12}$-alkyl, C$_5$–C$_8$-cycloalkyl, aryl, C$_7$–C$_{12}$-aralkyl, or C$_7$–C$_{12}$-alkylaryl, which comprises:

reacting a 3-(2'-oxyethyl)-dihydro-2(3H)furanone of the formula

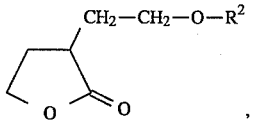

in which R$^2$ denotes C$_1$–C$_{12}$-alkyl, C$_5$–C$_8$-cycloalkyl, aryl, C$_7$–C$_{12}$-aralkyl, or C$_7$–C$_{12}$-alkylaryl, with a compound bearing the acyl group R$^1$CO—, where R$^1$ has the meanings given above, and being selected from the group consisting of carboxylic acids, carboxylic anhydrides and acyl halides, in the presence of an acid catalyst at a temperature of from 50° to 250° C. and a pressure of from 0.1 to 100 bar.

2. A process for the preparation of a 3-(2'-acyloxyethyl)-dihydro- 2(3H)furanone as claimed in claim 1, wherein the acid catalyst used is a mineral acid, a sulfonic acid, a zeolite, an alumosilicate, a heteropoly acid, an ion exchanger, a sulfonic acid attached to a polymeric support, a Lewis acid, or an acidic oxide.

3. A process for the preparation of a 3-(2'-acyloxyethyl)-dihydro- 2(3H)furanone as claimed in claim 1, wherein the acidic oxide used is silicon dioxide, titanium dioxide, zirconium dioxide, aluminum oxide.

4. A process for the preparation of a 3-(2'-acyloxyethyl)-dihydro- 2(3H)furanone as claimed in claim 1, wherein the reaction is carried out at a temperature of from 100° to 200° C.

5. A process for the preparation of a 3-(2'-acyloxyethyl)-dihydro-2(3H)furanone as claimed in claim 1, wherein the reaction is carried out under a pressure of from 1 to 10 bar.

6. A process as claimed in claim 1, wherein the furanone reactant II is 3-(2'-methoxyethyl)-dihydro-2(3H)furanone.

7. A process as claimed in claim 1, wherein the furanone reactant II is 3-(2'-tert.-butoxyethyl)-dihydro-2(3H)furanone.

8. A process as claimed in claim 1, wherein the furanone II is reacted with a carboxylic acid selected from the group consisting of formic acid, acetic acid, propionic acid, butyric acid, cyclohexanoic acid and benzoic acid.

9. A process as claimed in claim 1, wherein the molar ratio of the compound bearing an acyl group to the furanone II is from 1:1 to 10:1.

10. A process as claimed in claim 1, wherein the molar ratio of the compound bearing an acyl group to the furanone II is about 1.5:1.

11. A process as claimed in claim 1, wherein the acid catalyst is selected from the group consisiting of sulfuric acid, zeolites, toluenesulfonic acid and ion exchangers.

* * * * *

UNITED STATES PATENT AND TRADEMARK OFFICE
CERTIFICATE OF CORRECTION

PATENT NO. : 5,466,831
DATED : November 14, 1995
INVENTOR(S) : Schnurr et al.

It is certified that error appears in the above-identified patent and that said Letters Patent is hereby corrected as shown below:

Column 5, line 4, after "zirconium dioxide" delete "," and insert the word --or--.

Signed and Sealed this

Twentieth Day of February, 1996

Attest:

BRUCE LEHMAN

Attesting Officer     Commissioner of Patents and Trademarks